US011066352B2

(12) United States Patent
Pilsl et al.

(10) Patent No.: US 11,066,352 B2
(45) Date of Patent: Jul. 20, 2021

(54) PROCESSES OF MAKING L-ORNITHINE PHENYLACETATE

(71) Applicant: OCERA THERAPEUTICS, INC., Hazelwood, MO (US)

(72) Inventors: Ludwig Pilsl, Regensburg (DE); Georg Winkler, Regensburg (DE); Frank Demartin, Cary, NC (US); Vassil Elitzin, Lincoln, NE (US)

(73) Assignee: Ocera Therapeutics, Inc., Hazelwood, MO (US)

( * ) Notice: Subject to any disclaimer, the term of this patent is extended or adjusted under 35 U.S.C. 154(b) by 0 days.

(21) Appl. No.: 16/611,193

(22) PCT Filed: May 7, 2018

(86) PCT No.: PCT/US2018/031405
§ 371 (c)(1),
(2) Date: Nov. 5, 2019

(87) PCT Pub. No.: WO2018/208677
PCT Pub. Date: Nov. 15, 2018

(65) Prior Publication Data
US 2020/0157033 A1 May 21, 2020

Related U.S. Application Data

(60) Provisional application No. 62/504,911, filed on May 11, 2017.

(51) Int. Cl.
C07C 51/43 (2006.01)
C07C 229/26 (2006.01)
C07C 57/32 (2006.01)

(52) U.S. Cl.
CPC .............. C07C 51/43 (2013.01); C07C 57/32 (2013.01); C07C 229/26 (2013.01); C07B 2200/13 (2013.01)

(58) Field of Classification Search
None
See application file for complete search history.

(56) References Cited

U.S. PATENT DOCUMENTS

| 3,950,529 | A | 4/1976 | Fischer et al. |
| 4,100,293 | A | 7/1978 | Walser |
| 4,228,099 | A | 10/1980 | Walser |
| 4,284,647 | A | 8/1981 | Brusilow et al. |
| 4,320,146 | A | 3/1982 | Walser |
| 4,352,814 | A | 10/1982 | Walser |
| 4,457,942 | A | 7/1984 | Brusilow et al. |
| 5,139,981 | A | 8/1992 | Kurland |
| 5,405,761 | A | 4/1995 | Makryaleas et al. |
| 5,571,783 | A | 11/1996 | Montagne et al. |
| 5,591,613 | A | 1/1997 | Makryaleas et al. |
| 5,741,524 | A | 4/1998 | Staniforth et al. |
| 5,767,086 | A | 6/1998 | Kauvar et al. |
| 6,083,953 | A | 7/2000 | Nestor et al. |
| 6,258,849 | B1 | 7/2001 | Burzynski |
| 6,451,340 | B1 | 9/2002 | Arimilli et al. |
| 6,503,530 | B1 | 1/2003 | Kang et al. |
| 6,514,953 | B1 | 2/2003 | Armitage et al. |
| 6,768,024 | B1 | 7/2004 | Watson-Straughan et al. |
| 6,943,192 | B2 | 9/2005 | Burzynski |
| 8,173,706 | B2 * | 5/2012 | Anderson ............. C07C 229/26 514/576 |
| 8,389,576 | B2 | 3/2013 | Jalan et al. |
| 8,492,439 | B2 | 7/2013 | Anderson et al. |
| 8,785,498 | B2 | 7/2014 | Anderson et al. |
| 8,946,473 | B2 * | 2/2015 | Anderson ............. C07C 51/412 562/496 |
| 9,034,925 | B2 | 5/2015 | Anderson et al. |
| 9,260,379 | B2 | 2/2016 | Anderson et al. |
| 9,566,257 | B2 | 2/2017 | Jalan et al. |
| 9,604,909 | B2 | 3/2017 | Anderson et al. |
| 10,173,964 | B2 | 1/2019 | Anderson et al. |
| 10,550,069 | B2 | 2/2020 | Anderson et al. |
| 2003/0105104 | A1 | 6/2003 | Burzynski |
| 2003/0195255 | A1 | 10/2003 | Summar |
| 2004/0152784 | A1 | 8/2004 | March |
| 2004/0229948 | A1 | 11/2004 | Summar et al. |
| 2005/0059150 | A1 | 3/2005 | Guarino et al. |
| 2005/0182064 | A1 | 8/2005 | Burzynski |
| 2006/0045912 | A1 | 3/2006 | Truog |

(Continued)

FOREIGN PATENT DOCUMENTS

| AU | 2014250643 A1 | 11/2014 |
| AU | 2015221466 A1 | 9/2015 |

(Continued)

OTHER PUBLICATIONS

Abraldes et al., "Hemodynamic Response to Pharmacological Treatment of Portal Hypertension and Long-Term Prognosis of Cirrhosis", Hepatol. 2003, 37:902-908.

Aggarwal et al., "Predictors of Mortality and Resource Utilization in Cirrhotic Patients Admitted to the Medical ICU", Chest, 2001, vol. 119, Issue 5, pp. 1489-1497.

Albrecht et al., "Contrasting effects of thioacetamide-induced liver damage on the brain uptake indices of ornithine, arginine and lysine: modulation by treatment with ornithine aspartate", Metab Brain Dis., 1996, vol. 11, Issue 3, pp. 229-237.

Albrecht et al., "Increase of the brain uptake index for L-ornithine in rats with hepatic encephalopathy", Neuroreport., 1994, vol. 5, Issue 6, pp. 671-673.

(Continued)

Primary Examiner — Yong L Chu
(74) Attorney, Agent, or Firm — Knobbe, Martens, Olson & Bear, LLP

(57) ABSTRACT

Embodiments of the present disclosure are related to improved processes for making L-ornithine phenylacetate without using any silver salts or forming any L-ornithine intermediate salts, such as a benzoate salt. The present processes may be used in the commercial scale manufacturing of L-ornithine phenylacetate with high yields and low impurities.

18 Claims, No Drawings

(56) References Cited

U.S. PATENT DOCUMENTS

| | | |
|---|---|---|
| 2012/0157526 A1 | 6/2012 | Jalan et al. |
| 2014/0142186 A1 | 5/2014 | Scharschmidt et al. |
| 2016/0338982 A1 | 11/2016 | Ruettimann et al. |
| 2017/0135973 A1 | 5/2017 | Wang et al. |
| 2017/0189364 A1 | 7/2017 | Jalan et al. |
| 2018/0044281 A1 | 2/2018 | Anderson et al. |
| 2018/0161293 A1 | 6/2018 | Jalan et al. |
| 2018/0221320 A1 | 8/2018 | Rose et al. |
| 2018/0319736 A1 | 11/2018 | Anderson et al. |

FOREIGN PATENT DOCUMENTS

| | | |
|---|---|---|
| CA | 2763894 A1 | 1/2011 |
| CN | 1383815 | 12/2002 |
| CN | 101010087 A | 8/2007 |
| CN | 102993037 A | 3/2013 |
| EP | 1179347 | 2/2002 |
| EP | 1334722 | 8/2003 |
| EP | 1374863 | 1/2004 |
| EP | 1541141 | 6/2005 |
| FR | 2113774 A1 | 6/1972 |
| GB | 965637 | 8/1964 |
| GB | 1067742 | 5/1967 |
| GB | 1080599 | 8/1967 |
| GB | 1310658 | 3/1973 |
| GB | 1507951 | 4/1978 |
| JP | H05-221858 | 8/1993 |
| JP | 3273578 | 4/2002 |
| JP | S54-163518 | 12/2011 |
| MX | PA03009902 A | 5/2005 |
| WO | WO 1985/04805 | 11/1985 |
| WO | WO 1987/05297 | 9/1987 |
| WO | WO 1997/30167 | 8/1997 |
| WO | WO 2000/071151 | 11/2000 |
| WO | WO 2002/034255 | 5/2002 |
| WO | WO 2002/074302 | 9/2002 |
| WO | WO 2003/037378 | 5/2003 |
| WO | WO 2003/045372 | 6/2003 |
| WO | WO 2003/086074 | 10/2003 |
| WO | WO 2004/019928 | 3/2004 |
| WO | WO 2005/053607 | 6/2005 |
| WO | WO 2005/082023 | 9/2005 |
| WO | WO 2006/056794 | 6/2006 |
| WO | WO 2006/059237 | 6/2006 |
| WO | WO 2010/115055 | 10/2010 |
| WO | WO 2012/048043 | 4/2012 |
| WO | WO 2016/085887 | 6/2016 |

OTHER PUBLICATIONS

Al-Hassnan et al., "The relationship of plasma glutamine to ammonium and of glycine to acid-base balance in propionic acidaemia", J. Inherit. Metab. Dis., 2003, vol. 26, pp. 89-91.
Al Sibae et al., "Current Trends in the Treatment of Hepatic Encephalopathy", Ther Clin Risk Manag. Jun. 2009, 5(3): 617-626.
Als-Nielsen et al.,, Non-Absorbable Disaccharides for Hepatic Encephalopathy: Systematic Review of Randomised Trials, BMJ, 2004, p. 1-6.
Anadiotis et al., "Ornithine transcarbamylase deficiency and pancreatitis", J Pediatr, 2001, vol. 138, pp. 123-124.
Anonymous "Sodium phenylbutyrate for urea cycle enzyme deficiencies." [No authors listed], Med Lett Drugs Ther., Nov. 22, 1996, vol. 38, Issue 988, pp. 105-106.
Bachmann et al., "Ammonia toxicity to the brain and creatine", Molecular Genetics and Metabolism, 2004, vol. 81, pp. S52-S57.
Balata et al., "Induced hyperammonemia alters neuropsychology, brain MR spectroscopy and magnetization transfer in cirrhosis,", Hepatology, 2003, vol. 4, Issue 37, pp. 931-939.
Batshaw et al., "Alternative pathway therapy for urea cycle disorders: twenty years later", J Pediatr. 2001, 138(1 Suppl): S46-S55.
Batshaw et al., "Effect of sodium benzoate and sodium phenylacetate on brain serotonin turnover in the Ornithine transcarbamylase-deficient sparse-fur mouse", Pediatric Research, 1988, vol. 23, Issue 4, pp. 368-374.
Beale et al., "Early enteral supplementation with key pharmaconutrients improves sequential organ failure assessment score in critically ill patients with sepsis: outcome of a randomized, controlled, double blind trial,", Crit Care Med., 2008, vol. 1, Issue 36, pp. 131-144.
Berg et al., "Pharmacokinetics and cerebrospinal fluid penetration of phenylacetate and phenylbutyrate in the non-human primate", Cancer Chemother Pharmacol. May 2001, 47(5): 385-390. Abstract Only.
Berge et al., "Pharmaceutical Salts", J Pharm Sci, 1977, vol. 66, pp. 1-19.
Berry et al., "Long-term management of patients with urea cycle disorders", J Pediatri, 2001, vol. 138, Issue 1, pp. S56-S61.
Bighley et al., "Salt Forms of Drugs and Absorption" in Encyclopedia of Pharmaceutical Technology, Marcel Dekker, Inc. New York, 1996, pp. 453-499.
Blei et al., Pathophysiology of Cerebral Edema in Fulminant Hepatic Failure, Journal of Hepatology, 1999, p. 771-776, vol. 31, Denmark.
Bleichner, et al., "Frequency of infections in cirrhotic patients presenting with acute gastrointestinal haemorrhage", British Journal of Surgery, 1986, vol. 73, Issue 9, pp. 724-726.
Bongers et al., "Exogenous glutamine: the clinical evidence,", Crit Care Med., 2007, vol. 9 Suppl, Issue 35, pp. S545-S552.
Bosoi et al., Long term oral treatment of ornithine phenylacetate increases lean mass and attenuates brain edema in bile-duct ligated rats. Hepatology Oct. 2015, 62(Suppl 1):953A; Abstract 1523.
Braga et al., "Crystal Polymorphism and Multiple Crystal Forms", Struct Bond, 2009, 132: 25-50 [pub online Feb. 25, 2009].
Briggs et al., "Effect of Ornithine and Lactate on Urea Synthesis in Isolated Hepatocytes", Biochem J, 1976, vol. 160, pp. 205-209.
Bruha et al., "Effect of carvedilol on portal hypertension depends on the degree of endothelial activation and inflammatory changes", Scand J Gastroenter. 2006, 41: 1454-1463.
Brunquell et al., "Electroencephalographic findings in ornithine transcarbamylase deficiency", J Child Neurol, 1999, vol. 14, Issue 8, pp. 533-536.
Brusilow et al., "Amino acid acylation: A mechanism of nitrogen excretion in inborn errors of urea synthesis", Science, 1980, vol. 207, pp. 659-661.
Brusilow et al., "Treatment of episodic hyperammonemia in children with inborn errors of urea synthesis", The New England Journal of Medicine, 1984, vol. 310, Issue 25, pp. 1630-1634.
Burlina et al., "Long-term treatment with sodium phenylbutyrate in ornithine transcarbamylase-deficient patients", Molecular Genetics and Metabolism, 2001, vol. 72, pp. 351-355.
Butterworth, "Pathophysiology of hepatic encephalopathy: a new look at ammonia", Metab Brain Dis., 2002, vol. 17, Issue 4, pp. 221-227.
Butterworth, "Neuronal cell death in hepatic encephalopathy", Metab Brain Dis. Dec. 2007, 22(3-4): 309-320.
Byrn et al., "Pharmaceutical Solids: A Strategic Approach to Regulatory Considerations", Pharma Res. 1995, 12(7): 945-954.
Caira, M.R., "Crystalline Polymorphism of Organic Compounds", Topic in Current Chemistry 1998, 198: 163-208.
Callado França, et al., Five Days of Ceftriaxone to Treat Spontaneous Bacterial Peritonitis in Cirrhotic Patients, Journal of Gastroenterology, Feb. 2002, p. 119-122 vol. 37, No. 2, Springer, Japan.
Cavarec et al., "Molecular cloning and characterization of a transcription factor for the copia retrotransposon with homology to the BTB-Containing Lola Neurogenic Factor", Mol. Cell. Biol., 1997, vol. 17, Issue 1, pp. 482-494.
Chainuvati et al., "Ornicetil on encephalopathy. Effect of ornicetil (ornithine alpha-ketoglutarate) on encephalopathy in patients with acute and chronic liver disease", Acta Hepatogastro., 1977, vol. 24, Issue 6, pp. 434-439.
Chawla et al., "Challenges in Polymorphism of Pharmaeuticals", CRIPS Mar. 2004, 5(1): 9-12.
Chen et al., "Continuous arteriovenous hemodiafiltration in the acute treatment of hyperammonaemia due to ornithine transcarbamylase deficiency", Renal Failure, 2000, vol. 22, Issue 6, pp. 823-836.

(56) References Cited

OTHER PUBLICATIONS

Chung et al., "Cirrhosis and its Complications", Harrison's Principles of Internal Medicine (16th Edition) (2005) 289, pp. 1858-1869.
Clemmesen, et al., Cerebral Herniation in Patients With Acute Liver Failure is Correlated with Arterial Ammonia Concentration, Hepatology, Mar. 1999, p. 648-653, Vo. 29, No. 3, American Association for the Study of Liver Diseases.
ClinicalTrails.gov; William Lee, Med. Uni. S.C.; "Safety Study of Ornithine Phenylacetate to Treat Patients with Acute Liver Failure (STOP-ALF)", ID #NCT01548690; Feb. 2012; 7 pages.
Darmaun et al., "Phenylbutyrate-induced glutamine depletion in humans; effect on leucine metabolism", Am J Physiol Endocrinol Metab., 1998, vol. 274, pp. E801-E807.
Database WPI, Section CH, Week 200331, Derwent Publications Ltd., London, GB; XP002364873 & CN 1383815 A (Liu W), Dec. 11, 2002 (Abstract Only).
Davies, et al., "L-ornithine and phenylacetate synergistically produce sustained reduction in ammonia and brain water in cirrhotic rats", Hepatology Jul. 2009, 50(1): 155-164.
Dejong et al., "Altered glutamine metabolism in rat portal drained viscera and hindquarter during hyperammonemia", Gastroenterology, 1992, vol. 103, Issue 3, pp. 936-948.
Del Rosario et al., Hyperammonemic encephalopathy, J Clin Gastroenterol, 1997, vol. 25, Issue 4, pp. 682-684.
Desjardins et al., "Effect of portacaval anastomosis on glutamine synthetase protein and gene expression in brain, liver and skeletal muscle", Metab Brain Dis., 1999, vol. 14, Issue 4, pp. 273-280.
Dunitz et al., "Disappearing Polymorphs", Acc Chem Res. 1995, 28: 193-200.
Enns et al., "Survival after treatment with phenylacetate and benzoate for urea-cycle disorders,", N Engl J Med., 2007, vol. 22, Issue 356, pp. 2282-2292.
Fabbri et al., Unresponsiveness of Hepatic Nitrogen Metabolism to Glucagon Infusion in Patients with Cirrhosis: Dependence on Liver Cell Failure, Hepatology 1993, 18(1): 28-35.
Garcia-Tsao, MD, et al., Management and Treatment of Patients with Cirrhosis and Portal Hypertension: Recommendations from the Department of Veterans Affairs Hepatitis C Resource Center Program and the National Hepatitis C Program, Am J Gastroenterol, 2009, p. 1802-1829, Vo. 104.
Garden et al., "Prediction of outcome following acute variceal haemorrhage", Br J Surg., 1985, vol. 72, pp. 91-95.
Gebhardt et al., "Treatment of cirrhotic rats with L-Ornithine-L-Aspartate enhances urea synthesis and lowers serum ammonia levels", J Pharm Exp Thera., 1997, vol. 283, Issue 1, pp. 1-6.
Gonzalez-Navajas et al., "Bacterial DNA in patients with cirrhosis and sterile ascites. Its role as a marker of bacterial translocation and prognostic tool,", Rev Esp Enferm Dig., 2007, vol. 10, Issue 99, pp. 599-603.
Gordon, "Ornithine transcarbamylase deficiency: a urea cycle defect", European Journal of Paediatric Neurology, 2003, vol. 7, pp. 115-121.
Grace et al., "Prevention of initial variceal hemorrhage", Gastroenter Clin North Am., 1992, vol. 21, Issue 1, pp. 149-161.
Grant, D.J.W., "Theory and Origin of Polymorphism" Chapter 1 from Polymorphism in Pharmaceutical Solids, Brittain, Harry G. [Ed.]; Marcel Dekker, Inc., 1999; pp. 1-11.
Greenstein et al., Studies on the Metabolism of Amino Acids and Related Compounds in Vivo. III. Prevention of Ammonia Toxicity by Arginine and Related Compounds, Arch Biochem Biophys, 1956, vol. 64, Issue (2):, pp. 342-354.
Grossi et al., "Amino acids mixtures in prevention of acute ammonia intoxication in dogs", Arch Surg, 1967, vol. 94, pp. 261-266.
Guillory, J.K., "Generation of Polymorphs, Hydrates, Solvates, and Amorphous" Chapter 5 from Polymorphism in Pharmaceutical Solids, Brittain, Harry G. [Ed.]; Marcel Dekker, Inc., 1999, pp. 183-226.
Häberle et al., Hyperämmonamie: Ursachen, Diagnostik, Therapie, Dtsch Med Wochenschr, 2004, vol. 129; pp. 1430-1433.
Hamberg, Ole et al., Effects of an Increase in Protein Intake on Hepatic Efficacy for Urea Synthesis in Healthy Subjects and in Patients with Cirrhosis, Journal of Hepatology, 1992, pp. 237-243, Elsevier Science Publishers B.V.
Hass et al., "Detection of subclinical and overt hepatic encephalopathy and treatment control after L-Ornithine-L-Aspartate medication by magnetic resonance spectroscopy (1H-MRS)", Z Gastroenterol, 2005, vol. 43, pp. 373-378.
Häussinger et al., "Hepatic encephalopathy in chronic liver disease: a clinical manifestation of astrocyte swelling and low-grade cerebral edema?", J Hepatol., 2000, vol. 32, Issue 6, pp. 1035-1038.
Herlong et al., "The use of ornithine salts of branched-chain ketoacids in portal-systemic encephalopathy", Ann Intern Med., 1980, vol. 93, Issue 4, pp. 545-550.
Hirayama et al., [Eds], "Organic compound crystal produced handbook—Principles and know-how", Maruzen Co., Ltd., Japan; (Jul. 2008), pp. 17-23, 37-40, 45-51 and 57-65; 31 pages.
Honda et al., "Successful treatment of severe hyperammonemia using sodium phenylacetate powder prepared in hospital pharmacy", Biol. Pharm. Bull., Sep. 2002, 25(9): 1244-1246.
Hopkins Medicine (http://www.hopkinsmedicine.org/gastroenterology_hepatology/_pdfs/liver/portal hypertension.pdf; accessed Jun. 22, 2016); 13 pages.
Hursthouse et al., "Why Do Organic Compounds Crystallise Well or Badly or Ever so Slowly? Why is Crystallisation Nevertheless Such a Good Purification Technique?", Organic Process Research & Development, 2009, 13:1231-1240.
Igarashi et al., "Determination of ornithine conjugates of some carboxylic acids in birds by high-performance liquid chromatography", Chem Pharm Bull, 1992, vol. 40, Issue 8, pp. 2196-2198.
Inoue et al., "Biochemical analysis of decreased ornithine transport activity in the liver mitochondria from patients with hyperornithinemia, hyperammonemia and homocitrullinuria", Biochim Biophys Acta., 1988, vol. 964, Issue 1, pp. 90-95.
Iyer et al., "Mouse model for human arginase deficiency", Mol Cell Biol., 2002, vol. 22, Issue 13, pp. 4491-4498.
Jalan et al., "Acute-on-chronic liver failure: pathophysiological basis of therapeutic options", Blood Purif, 2002, vol. 20, pp. 252-261.
Jalan et al., "Moderate hypothermia in patients with acute liver failure and uncontrolled intracranial hypertension,", Gastroenterology, 2004, vol. 5, Issue 127, pp. 1338-1346.
Jalan et al., "The molecular pathogenesis of hepatic encephalopathy", The International Journal of Biochemistry & Cell Biology, 2003, vol. 35, pp. 1175-1181.
Jalan et al., L-Ornithine Phenylacetate (OP): A Novel Treatment for Hyperammonemia and Hepatic Encephalopathy, Medical Hypotheses, 2007, 69(5): 1064-1069, Elsevier Ltd.
Jalan et al., Treatment of Hyperammonemia in Liver Failure: A Tale of Two Enzymes, Gastroenterology, 2009, p. 2048-2051, vol. 1236.
Jalan Intracranial Hypertension in Acute Liver Failure: Pathophysiological Basis of Rational Management, Seminars in Liver Disease, 2003, p. 271-282, vol. 23, No. 3, Thieme Medical Publisheres, Inc., New York, NY, USA.
James et al., "The conjugation of phenylacetic acid in man, sub-human primates and some non-primate species", Proc R Soc Lond B., 1972, vol. 182, pp. 25-35.
Jeyamani et al., Hepatitis E virus and acute-on-chronic liver failure,, Indian J Gastroentero., 2004, vol. 23, Issue 2, pp. 45-46.
Jiang et al., "L-Ornithine-l-aspartate in the management of hepatic encephalopathy: a meta-analysis", J Gastroenterol Hepatol. 2009, 24(1): 9-14; available online: Sep. 28, 2008.
Jover-Cobos et al., Ornithine phenylacetate revisited; Metabolic Brain Disease 2013, 28(2): 327-331.
Kaiser, S. et al., Ammonia and Glutamine Metabolism in Human Liver Slices: New Aspects on the Pathogenesis of Hyperammonaemia in Chronic Liver Disease, European journal of Clinical Investigation , 1988, vol. 18, pp. 535-542.
Kasumov et al., "New secondary metabolites of phenylbutyrate in humans and rats", Drug Metab Dispos., 2004, vol. 32, Issue 1, pp. 10-19.
Katayama, "Ammonia metabolism and hepatic encephalopathy", Hep. Research, 2004, vol. 30, Issue 1, pp. S71-S78.

(56) References Cited

OTHER PUBLICATIONS

Khan et al.,, Frequency of Spontaneous Bacterial Peritonitis in Cirrhotic Patients with Ascites Due to Hepatitis C Virus and Efficacy of Ciprofloxacin in its Treatment, Gomal Journal of Medical Sciences, Jul.-Dec. 2009, p. 149-154, vol. 7, No. 2.

Kircheis et al., "Therapeutic efficacy of L-ornithine-L-aspartate infusions in patients with cirrhosis and hepatic encephalopathy: results of a placebo-controlled, double blind study,", Hepatology, 1997, vol. 6, Issue 25, pp. 1351-1360.

Kojima et al., "Effective Solid Form Selection for the Pharmaceutical Development", J Pharma Science Tech. Sep. 2008, 68(5): 344-349.

Larsen et al., "Alternative Pathway Therapy for Hyperammonemia in Liver Failure"; Hepatolory, Jul. 2009, 50(1): 3-5.

Lee et al., Acute Liver Failure: Summary of a Workshop, Hepatology, Apr. 2008, p. 1401-1415, vol. 47, No. 4.

Lee, W. M., Acetaminophen-Related Acute Liver Failure in the United States, Hepatology Research, 2008, p. S3-S8, vol. 38, Suppl. 1, The Japan Society of Hepatology.

Linderoth et al., "Short-term prognosis of community-acquired bacteremia in patients with liver cirrhosis or alcoholism: A population-based cohort study,", Alcohol Clin Exp Res., 2006, Issue 30, pp. 636-641.

Lopez-Talavera et al., "Thalidomide Inhibits Tumor Necrosis Factor alpha, Decreases Nitric Oxide Synthesis, and Ameliorates the Hyperdynamic Circulatory Syndrome in Portal-Hypertensive Rats", Hepatology, 1996, 23(6): 1616-1621.

Lukkarinen, M. et al., Effect of Lysine Infusion on Urea Cycle in Lysinuric Protein Intolerance, Metabolism, May 2000, 49(5): 621-625.

Lukkarinen, M. et al., Oral Supplementation Corrects Plasma Lysine Concentrations in Lysinuric Protein Intolerance, Metabolism, Jul. 2003, 52(7): 935-938.

MacArthur et al., "Pharmacokinetics of sodium phenylacetate and sodium benzoate following intravenous administration as both a bolus and continuous infusion to healthy adult volunteers", Molecular Genetics and Metabolism, 2004, vol. 81, pp. S67-S73.

Maestri et al., "Long-term treatment of girls with ornithine transcarbamylase deficiency", N Engl J Med., 1996, vol. 335, Issue 12, pp. 855-859.

Maestri et al., "Prospective treatment of urea cycle disorders", J Pediatr., 1991, vol. 119, Issue 6, pp. 923-928.

Maev I.V. Application of L-ornitine-L-aspartate in complex therapy of hepatic encephalopathy in liver cirrhosis patients (Engl. Title) koloproktologii, 2002, No. 6, pp. 60-66.

Maier et al., Originalien Activities of Urea-Cycle Enzymes in Chronic Liver Disease, Klinische-Wochenschrift, 1979, vol. 67, pp. 661-665, Springer-Verlag.

Maier, "Therapie der hepatischen Enzephalopathie", Dtsch med Wschr., 1988, vol. 113, pp. 1886-1889.

Maruzen Co., Ltd., "Jikken Kagaku Guide Book (Experimental Chemistry Guide Book)," The Chemical Society of Japan, 1992, 3rd Edition, pp. 130-131.

Maruzen Co., Ltd., "Jikken Kagaku Koza (Zoku) Experimental Chemistry Course (cont.)", 2. Bunri to Seisei (Isolation and Purification), Jan. 25, 1967, pp. 159-162 and 184-193.

Matsuoka et al., "Advanced Crystallization Technology of Organic Materials—Control of Size, Morphology, Polymorph and Purity", Pharm Tech, Japan (May 2003) 19(6): 91(955)-101(965).

Meijer et al., Nitrogen Metabolism and Ornithine Cycle Function, Physiological Reviews, Jul. 1990, vol. 70, No. 3, pp. 701-748, The American Physiological Society.

Mendenhall et al., "A new therapy for portal systemic encephalopathy", The American Journal of Gastroenterology, 1986, vol. 81, Issue 7, pp. 540-543.

Mihm et al., "Effect of L-ornithine-L-aspartate (LOLA) on neurometabolites in hepatic encephalopathy (HE)", Hepatology, 2001, vol. 34, Issue 4, pp. 543A.

Mizock et al., "Septic Encephalopathy—Evidence for altered phenylalanine metabolism and comparison with hepatic encephalopathy", Arch Intern Med, 1990, vol. 150, pp. 443-449.

Mizock, Nutritional Support in Hepatic Encephalopathy, Nutrition, 1999, pp. 220-228, vol. 15, No. 3, Elsevier Science Inc.

Mizutani et al., "Hyperargininemia: Clinical course and treatment with sodium benzoate and phenylacetic acid", Brain Dev., 1983, vol. 5, Issue 6, pp. 555-563.

Mohamed et al., "Effect of toll-like receptor 7 and 9 targeted therapy to prevent the development of hepatocellular carcinoma", Liver Int. Mar. 2015, 35(3): 1063-1076.

Mohammad R.A. et al., Combination therapy for the treatment and prevention of hepatic encephalopathy; Ann Pharmacother. (Nov. 2012) 46(11): 1559-1563.

Moinard et al.,, "Effects of Ornithine 2-Oxoglutarate on Neutrophils in Stressed Rates: Evidence for the Involvement of Nitric Oxide and Polyamines", Clin Sci, 2002, vol. 102, Issue 3, pp. 287-295, London, England.

Mokhtarani, M. et al., "Urinary Phenylacetylglutamine as Dosing Biomarker for Patients with Urea Cycle Disorders", Mol Genet Metab. (Nov. 2012) 107(3): 308-314.

Mookerjee et al., "Neutrophil dysfunction in alcoholic hepatitis superimposed on cirrhosis is reversible and predicts the outcome,", Hepatology, 2007, vol. 3, Issue 46, pp. 831-840.

Mookerjee et al., "Increased gene and protein expression of the novel eNOS regulatory protein NOSTRIN and a variant in alcoholic hepatitis", Gastroenterology Jun. 2007, 132(7): 2533-2541.

Mouille et al., "Adaptative increase of ornithine production and decrease of ammonia metabolism in rat colonocytes after hyperproteic diet ingestion", Am J Gastrointest Liver Physiol., 2004, 287(2), G344-G351.

Nance et al., "Ammonia production in germ-free Eck fistula dogs", Surgery, 1971, vol. 70, Issue 2, pp. 169-174.

Navasa et al., "Bacterial infections in liver cirrhosis,", Ital J Gastroenterol Hepatol., 1999, vol. 7, Issue 31, pp. 616-625.

Nema et al., "Excipients and Their Role in Approved Injectable Products: Current Usage and Future Directions", PDA J Pharm Sci Technol. 2011, 65(3): 287-332.

Newsholme et al., "Glutamine metabolism by lymphocytes, macrophages, and neutrophils: its importance in health and disease,", J Nutr Biochem., 1999, vol. 6, Issue 10, pp. 316-324.

Newsholme, "Why is L-glutamine metabolism important to cells of the immune system in health, postinjury, surgery or infection?", J Nutr., 2001, vol. 9 Suppl, Issue 131, pp. 2515S-2522S.

Ocera Therapeutics, Inc., News Release: Ocera Completes Interim Analysis of OCR-002 in Phase 2b STOP-HE Study for the Treatment of Acute Hepatic Encephalopathy; Globe Newswire; Apr. 1, 2015, 2 pages.

Ocera Therapeutics, Inc., News Release: Ocera Announces Positive Phase 1 Results for Oral OCR-002 in Development for the Prevention of Acute Hepatic Encephalopathy; Globe Newswire; Nov. 16, 2015, 2 pages.

Ocera Therapeutics, Inc., News Release: Ocera Completes Plasma Data from Pilot Phase 1 Study for Orally-available OCR-002 in Development for the Prevention of Acute Hepatic Encephalopathy; Globe Newswire; Jan. 8, 2016, 3 pages.

Olde Damink et al., "Decreased plasma and tissue isoleucine levels after simulated gastrointestinal bleeding by blood gavages in chronic portacaval shunted rats", Gut, 1997, vol. 40, pp. 418-424.

Olde Damink et al., "Interorgan ammonia and amino acid metabolism in metabolically stable patients with cirrhosis and a TIPSS", Hepatology, 2002, vol. 36, Issue 5, pp. 1163-1171.

Olde Damink et al., "Interorgan ammonia metabolism in liver failure", Neurochemistry International, 2002, vol. 41, pp. 177-188.

Olde Damink et al., "The kidney plays a major role in the hyperammonemia seen after simulated or actual GI bleeding in patients with cirrhosis", Hepatology, 2003, vol. 37, pp. 1277-1285.

Olde Damink et al., Stimulated Liver and Muscle Protein Synthesis by Intravenous Isoleucine Supplementation During a Simulated Variceal Bleed in Patients with Cirrhosis of the Liver, Hepatology, Oct. 2001, AASLD Abstracts #50.

(56) References Cited

OTHER PUBLICATIONS

Pauwels et al., "Systemic antibiotic prophylaxis after gastrointestinal hemorrhage in cirrhotic patients with a high risk of infection", Hepatology, 1996, vol. 24, Issue 4, pp. 802-806.
Petrowski et al., "Pharmacologic amino acid acylation in the acute hyperammonemia of propionic acidemia", Journal of Neurogenetics, 1987, vol. 4, pp. 87-96.
Plecko et al., "Partial N-acetylglutamate synthetase deficiency in a 13-year-old girl: diagnosis and response to treatment with N-carbamylglutamate", Eur J Pediatr., 1998, vol. 157, pp. 996-998.
Powell et al., "Compendium of Excipients for Parenteral Formulations", PDA J Pharm Sci Technol. 1998, 52(5): 238-311.
Praphanphoj et al., "Three cases of intravenous sodium benzoate and sodium phenylacetate toxicity occurring in the treatment of acute hyperammonemia", J Inherit Metab Dis., 2000, vol. 23, pp. 129-136.
Rajkovic et al., "Mechanisms of abnormalities in host defences against bacterial infection in liver disease,", Clin Sci. (Lond.), 1985, vol. 3, Issue 68, pp. 247-253, London.
Ramaswamy et al., "Mouse model for human arginase deficiency", Mol Cell Biol., Jul. 2002, vol. 22, Issue 13, pp. 4491-4498.
Rees et al., "Effect of L-Ornithine-L-Aspartate on patients with and without TIPS undergoing glutamine challenge: a double blind, placebo controlled trial", Gut, 2000, vol. 47, pp. 571-574.
Riordan et al., "Treatment of hepatic encephalopathy", Curr Concepts, 1997, vol. 337, Issue 7, pp. 473-479.
Rockey et al., "Randomized, Double-Blind, Controlled Study of Glycerol Phenylbutyrate in Hepatic Encephalopathy," Hepatology (2014) 59(3): 1073-1083.
Rogers, Q. R. et al., Deficiency of Pyrroline-5-Carboxylate Synthase in the Intestinal Mucosa of the Cat, J Nutrition, 1985, 115(1): 146-150.
Romero-Gómez et al., "Intestinal glutaminase activity is increased in liver cirrhosis and correlates with minimal hepatic encephalopathy", J Hepatol. 2004, 41: 49-54.
Rose et al., "L-Ornithine-L-Aspartate in experimental portal-systemic encephalopathy: therapeutic efficacy and mechanism of action", Metabolic Brain Disease, 1998, vol. 13, Issue 2, pp. 147-157.
Rose et al., "L-Ornithine-L-Aspartate lowers plasma and cerebrospinal fluid ammonia and prevents brain edema in rats with acute liver failure", Hepatology, 1999, vol. 30, Issue 3, pp. 636-640.
Rudman et al., Maximal Rates of Excretion and Synthesis of Urea in Normal and Cirrhotic Subjects, The Journal of Clinical Investigation, Sep. 1973, vol. 52, pp. 2241-2249.
Rukmini et al., "Region-specific changes in CNS muscarinic acetylcholine receptors in a rat model of hyperammonemia", Biochem Pharmacol., 1998, vol. 56, Issue 2, pp. 237-241.
Sanyal et al., Portosystemic Encephalopathy After Transjugular Intrahepatic Portosystemic Shunt: Results of a Prospective Controlled Study, Hepatology, 1994, p. 46-55, vol. 20, No. 1, Pt. 1, The American Association for the Study of Liver Diseases.
Sanyal, A. J., Prediction of Variceal Hemorrhage in Patients with Cirrhosis, UpToDate, Inc., Website (www.uptodate.com), Jan. 2010, UpToDate.
Sarhan et al., "Effects of inhibition of ornithine aminotransferase on thioacetamide-induced hepatogenic encephalopathy", Neurochem Res., 1993, vol. 18, Issue 4, pp. 539-549.
Scaglia et al., "Effect of alternative pathway therapy on branched chain amino acid metabolism in urea cycle disorder patients", Mol Genet Metabolism, 2004, vol. 81, pp. S79-S85.
Sears et al., "Disruption of the blood-brain barrier in hyperammonaemic coma and the pharmacologic effects of dexamethasone and difluoromethyl ornithine", J Neurosci Res., 1985, vol. 14, Issue 2, pp. 255-261.
Seiler et al., "Ornithine aminotransferase activity, liver ornithine concentration and acute ammonia intoxication", Life Sciences, 1989, vol. 45, Issue 11, pp. 1009-1020.
Seiler, "Ornithine aminotransferase, a potential target for the treatment of hyperammonemias", Curr Drug Targets., Sep. 2000, vol. 1, Issue 2, pp. 119-153.
Sen et al., "The pathophysiological basis of acute-on-chronic liver failure", Liver, 2002, vol. 22, Issue Suppl. 2, pp. 5-13.
Shangraw et al., Effect of Liver Disease and Transplantation on Urea Synthesis in Humans: Relationship to Acid-Base Status, Am J Physiol Gastrointest Liver Physiol, 1999, vol. 276, pp. 1145-1152.
Shawcross et al., "Ammonia impairs neutrophil phagocytic function in liver disease,", Hepatology, 2008, vol. 4, Issue 48, pp. 1202-1212.
Shawcross et al., "Dispelling myths in the treatment of hepatic encephalopathy,", Lancet, 2005, vol. 9457, Issue 365, pp. 431-433.
Shawcross et al., "Hyperammonemia impairs neutrophil function", Hepatology, 2005, vol. 42, pp. 537A.
Shriner et al., "Recrystallization", Chapter 3.5 Preliminary Examination in the Systematic Identification of Organic Compounds, John Wiley & Sons, Inc. New York, 1998, Chapter 3, pp. 78-81.
Simell et al., "Waste nitrogen excretion via amino acid acylation: benzoate and phenylacetate in lysinuric protein intolerance", Pediatric Research, 1986, vol. 20, Issue 11, pp. 1117-1121.
Singh, et al., Changing Epidemiology and Predictors of Mortality in Patients With Spontaneous Bacterial Peritonitis at a Liver Transplant Unit, Clinical Microbiology and Infection, Jun. 2003, p. 531-537, vol. 9, No. 6., European Society of Clinical Microbiology and Infectious Diseases.
Smith et al., "The treatment of inborn errors of the urea cycle", Nature, 1981, vol. 291, Issue 5814, pp. 378-380.
Solaini et al., "Variations in the plasma concentration of ornithine, citrulline and arginine in acute experimental liver failure" [Article in Italian], Boll Soc Ital Biol Sper., 1981, vol. 57, Issue 7, pp. 705-710.
Stedman's Medical Dictionary; "Encephalopathy", 27th Edition, 2002; 1 page.
Stewart, P. M., et al., Effects of Arginine-Free Meals on Ureagenesis in Cats, American Journal of Physiology, 1981, pp. E310-E315, vol. 241, No. 4, The American Physiological Society.
Stravitz, MD, et al., Intensive Care of Patients with Acute Liver Failure: Recommendations of the U.S. Acute Liver Failure Study Group, Critical Care Medicine, 2007, p. 2498-2508, vol. 35, No. 11, Lippincott Williams & Wilkins.
Suchy et al., Clinical Manifestations and Complications—Typical Clinical Presentation;, Liver Disease in Children, 2nd Edition, 2001, pp. 74-77.
Sugarbaker et al., "The role of the small intestine in ammonia production after gastric blood administration", Ann Surg., 1987, vol. 206, Issue 1, pp. 5-17.
Sukhotnik et al., "Oral glutamine prevents gut mucosal injury and improves mucosal recovery following lipopolysaccharide endotoxemia in a rat,", J Surg Res., 2007, vol. 2, Issue 143, pp. 379-384.
Svanberg et al., "Effects of amino acids on synthesis and degradation of skeletal muscle proteins in humans", Am J Physiol., 1996, vol. 271, Issue 4 Pt1, pp. E718-E724.
Timely Data Resource (TDR), IPD Printable Search Results, "Incidence and Prevalence Database, ICD-9 Code: 567. Peritonitis," <URL:http://www.tdrdata.com/IPD/ipd_searchresultsdataprinter.aspx?SessionGUID=ac0c91d8-7 . . . , Jul. 27, 2010, 7 pages.
Teran et al., "Primary prophylaxis of variceal bleeding in cirrhosis: A cost-effectiveness analysis", Gastroenter., 1997, vol. 112, Issue 2, pp. 473-482.
Trebicka et al., Atorvastatin lowers portal pressure in cirrhotic rats by inhibition of RhoA/Roh-kinase and activation of endothelial nitric oxide synthase, Hepatology, 2007, 46(1): 242-253.
Tuchman, M., et al., Management of Inherited Disorders of Ureagenesis, The Endocrinologist, 2002, vol. 12, No. 2, p. 99-109.
Tuchman, MD et al., "Episodic hyperammonemia in adult siblings with hyperornithinemia, hyperammonemia, and homocitrullinuria syndrome", Arch Neurol., 1990, vol. 47, pp. 1134-1137.
Van Berlo et al., "Is increased ammonia liberation after bleeding in the digestive tract the consequence of complete absence of isoleucine in hemoglobin? A study in pigs", Hepatology, 1989, vol. 10, Issue 3, pp. 315-323.

(56) References Cited

OTHER PUBLICATIONS

Van Den Berg et al., "The effect of glutamine-enriched enteral nutrition on intestinal microflora in very low birth weight infants: a randomized controlled trial,", Clin Nutr., 2007, vol. 4, Issue 26, pp. 430-439.

Vilstrup, H. et al., Elimination of Infused Amino Acids From Plasma of Control Subjects and of Patients With Cirrhosis of the Liver, European Journal of Clinical Investigation, 1982, vol. 12, pp. 197-202, Blackwell Scientific Publications.

Vogels et al., "L-ornithine vs L-ornithine-L-aspartate as a treatment for hyperammonemia-induced encephalopathy in rats", J Hepatology, 1997, vol. 26, Issue 1, pp. 174-182.

Wasmuth et al., "Patients with acute on chronic liver failure display 'sepsis-like' immune paralysis,", J Hepatol., 2005, vol. 2, Issue 42, pp. 195-201.

Wright et al., "Reduction in Ammonia with L-Ornithine, Phenylacetate (OP) but not Anti-TNF Prevents LPS Induced Brain Edema in Bile-duct Ligated Cirrhotic Rats", Abstract 773; J Hepatology 2009, 50: S283.

Ytrebø et al., "Interorgan ammonia, glutamate, and glutamine trafficking in pigs with acute liver failure,", Am J Physiol Gastrointest Liver Physiol., 2006, vol. 3, Issue 291, pp. G373-G381.

Ytrebø et al., "L-Ornithine Phenylacetate Attenuates Increased Arterial and Extracellular Brain Ammonia and Prevents Intracranial Hypertension in Pigs with Acute Liver Failure", Hepatology, Jul. 2009, 50(1): 165-174.

Yudkoff et al., "In Vivo Nitrogen Metabolism in Ornithine Transcarbamylase Deficiency", J Clin. Invest., Nov. 1996, 98(9): 2167-2173.

Zetterman, Rowen K., MD, "Complications of Portal Hypertension: Hepatic Encephalopathy", Medscape (Jun. 2011) available online at www.medscape.com/viewarticle/744392; downloaded Dec. 3, 2014; 6 pages.

Zieve et al., "Ammonia toxicity: comparative protective effect of various arginine and ornithine derivatives, aspartate, benzoate, and carbamyl glutamate", Metabo Brain Dis., 1986, vol. 1, Issue 1, pp. 25-35.

Zieve et al., "Conditional deficiencies of ornithine or ornithine or arginine", J Am Coll Nutr., 1986, vol. 5, Issue 2, pp. 167-176.

Ventura-Cots et al., Safety of ornithine phenylacetate in cirrhotic decompensated patients: an open-label, dose-escalating, single-cohort study; J Clin Gastroenter. (2013) 47(10): 881-887.

International Search Report and Written Opinion dated Aug. 1, 2018 for PCT/US2018/031405, filed May 7, 2018.

* cited by examiner

PROCESSES OF MAKING L-ORNITHINE PHENYLACETATE

INCORPORATION BY REFERENCE TO PRIORITY APPLICATIONS

The present application is the U.S. national phase under 35 U.S.C. § 371 of International Application No. PCT/US2018/031405, filed May 7, 2018, which designates the United States and claims the benefit of priority to U.S. Provisional Application No. 62/504,911, filed May 11, 2017, which is incorporated by reference in its entirety.

BACKGROUND

Field

The present disclosure relates to the fields of pharmaceutical chemistry, biochemistry, and medicine. In particular, it relates to processes of making L-ornithine phenylacetate, compositions and methods of using the same.

Description

Hyperammonemia is a hallmark of liver disease and is characterized by an excess of ammonia in the bloodstream. Hepatic encephalopathy is a primary clinical consequence of progressive hyperammonemia and is a complex neuropsychiatric syndrome, which may complicate acute or chronic hepatic failure. It is characterized by changes in mental state including a wide range of neuropsychiatric symptoms ranging from minor signs of altered brain function to overt psychiatric and/or neurological symptoms, or even deep coma. The accumulation of unmetabolized ammonia has been considered as the main factor involved in the pathogenesis of hepatic encephalopathy, but additional mechanisms may be associated.

L-Ornithine monohydrochloride and other L-ornithine salts are available for their use in the treatment of hyperammonemia and hepatic encephalopathy. For example, U.S. Publication No. 2008/0119554, which is hereby incorporated by reference in its entirety, describes compositions of L-ornithine and phenylacetate for the treatment of hepatic encephalopathy. L-ornithine has been prepared by enzymatic conversion methods. For example, U.S. Pat. Nos. 5,405,761 and 5,591,613, both of which are hereby incorporated by reference in their entirety, describe enzymatic conversion of arginine to form L-ornithine salts. Sodium phenylacetate is commercially available, and also available as an injectable solution for the treatment of acute hyperammonemia. The injectable solution is marketed as AMMONUL.

Although salt forms may exhibit improved degradation properties, certain salts, particularly sodium or chloride salts, may be undesirable when treating patients having diseases associated with the liver disease, such as hepatic encephalopathy. For example, a high sodium intake may be dangerous for cirrhotic patients prone to ascites, fluid overload and electrolyte imbalances. Similarly, certain salts are difficult to administer intravenously because of an increased osmotic pressure, i.e., the solution is hypertonic. High concentrations of excess salt may require diluting large volumes of solution for intravenous administration which, in turn, leads to excessive fluid overload. Accordingly, there exists a need for the preparation of L-ornithine and phenylacetate salts which are favorable for the treatment of hepatic encephalopathy or other conditions where fluid overload and electrolyte imbalance are prevalent.

SUMMARY

Some embodiments of the present disclosure include a process of making L-ornithine phenylacetate, comprising: intermixing L-ornithine hydrochloride and potassium hydroxide in a first solvent to form a first reaction mixture; adding a second solvent to said first reaction mixture, isolating potassium chloride from said first reaction mixture; intermixing phenylacetic acid with said first reaction mixture to form a second reaction mixture; and isolating a composition comprising L-ornithine phenylacetate from said second reaction mixture. In some embodiments, the process further comprises stirring the first reaction mixture. In some embodiments, the process further comprises cooling said first reaction mixture before isolating potassium chloride. In some embodiments, the process further comprises recrystallizing the composition comprising L-ornithine phenylacetate.

Some embodiments of the present disclosure include a composition comprising L-ornithine phenylacetate prepared by the process disclosed herein.

Some embodiments of the present disclosure include a composition comprising L-ornithine phenylacetate having a chloride content of less than about 1.5% by weight, wherein the composition is free of silver ion, benzoic acid or salts thereof. In some embodiments, the composition is free of L-ornithine cyclization or dimerization side products.

DETAILED DESCRIPTION

Disclosed herein are processes of making L-ornithine phenylacetate, and in particular, large scale and high efficiency processes of making L-ornithine phenylacetate. These processes permit large-scale production of pharmaceutically acceptable forms of L-ornithine phenylacetate using economical processes. Moreover, the processes of making L-ornithine phenylacetate have the added benefit of having low amounts of impurities.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, formulation, or device, the term "comprising" means that the compound, composition, formulation, or device includes at least the recited features or components, but may also include additional features or components.

As used herein, common organic abbreviations are defined as follows:

hr Hour(s)
IPC In-process control
IR Immediate release
KCl Potassium chloride
KOH Potassium hydroxide
ORN Ornithine
PAA Phenylacetic acid
PAGN Phenylacetylglutamine The term "immediate release" as used herein, has its ordinary meaning as understood by those skilled in the art and thus includes, by way of non-limiting example, release of a drug from a dosage form in a relatively brief period of time after administration.

The term "controlled release" and the term "extended release" as used herein, each has its ordinary meaning as understood by those skilled in the art and thus includes, by way of non-limiting example, controlled release of a drug from a dosage form over an extended period of time. For example, in some embodiments, controlled release or extended release formulations are those that have a release rate that is substantially longer than that of a comparable immediate release form. The two terms can be used interchangeably.

The term "about" as used herein, refers to a quantity, value, number, percentage, amount, or weight that varies from the reference quantity, value, number, percentage, amount, or weight by a variance considered acceptable by one of ordinary skill in the art for that type of quantity, value, number, percentage, amount, or weight. In various embodiments, the term "about" refers to a variance of 20, 15, 10, 9, 8, 7, 6, 5, 4, 3, 2 or 1% relative to the reference quantity, value, number, percentage, amount, or weight.

The term "oral dosage form" as used herein, has its ordinary meaning as understood by those skilled in the art and thus includes, by way of non-limiting examples, a formulation of a drug or drugs in a form orally administrable to a human, including pills, tablets, cores, capsules, caplets, loose powder, liquid solution or suspension.

The term "phenylacetic acid" as used herein, is also known as benzeneacetic acid or 2-phenylacetic acid). It has the following chemical structure:

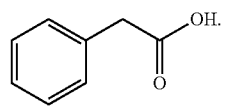

The term "phenylacetate" as used herein, refers to the anionic form of phenylacetic acid with the following chemical structure:

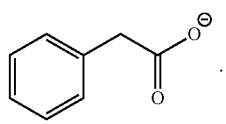

The term "L-ornithine phenylacetate" as used herein, refer to a compound consisting of L-ornithine cation and phenylacetate anion. It has the following chemical structure:

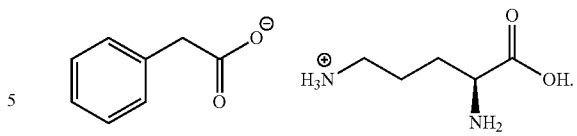

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions or formulations is contemplated. Supplementary active ingredients can also be incorporated into the compositions or formulations. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic cations from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine Many such salts are known in the art, as described in WO 87/05297, Johnston et al., published Sep. 11, 1987 (incorporated by reference herein in its entirety).

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

"Treat," "treatment," or "treating," as used herein refers to administering a pharmaceutical composition/formulation for prophylactic and/or therapeutic purposes. The term "prophylactic treatment" refers to treating a patient who is not yet suffering from a disease, but who is susceptible to, or otherwise at risk of, a particular disease, whereby the treatment reduces the likelihood that the patient will develop a disease. The term "therapeutic treatment" refers to administering treatment to a patient already suffering from a disease.

Processes of Manufacturing L-Ornithine Phenylacetate

Some embodiments of the present disclosure relate to processes of making L-ornithine phenylacetate. The processes can be used in the large scale manufacturing of L-ornithine phenylacetate, and easily scalable without significant amounts of impurities, such as chloride ions, or side products, such as L-ornithine cyclization or dimerization side products. Additionally, the processes advantageously eliminate the use of costly purification techniques, such as azeotropic distillation or chromatography. Accordingly, the present processes of making L-ornithine phenylacetate allow for greater economy and purity in the large scale production of L-ornithine phenylacetate.

Some embodiments of the present disclosure relate to compositions of L-ornithine phenylacetate with low concentrations of impurities and side products. Impurities and side products in an L-ornithine phenylacetate salt composition may limit the commercial availability of the composition, due their harmful or dangerous effects in some patients. Impurities may be derived from salts used in the process of making L-ornithine phenylacetate, such as chloride ion, benzoate, silver ion, etc. Side products may be due to cyclization or dimerization reactions, such as cyclization or dimerization of L-ornithine. Accordingly, the present compositions of L-ornithine phenylacetate provide significant improvements, and allow for their medical use in broader patient populations.

Some embodiments of the present disclosure include a process of making L-ornithine phenylacetate, comprising: intermixing L-ornithine hydrochloride and potassium hydroxide in a first solvent to form a first reaction mixture; adding a second solvent to said first reaction mixture, isolating potassium chloride from said first reaction mixture; intermixing phenylacetic acid with said first reaction mixture to form a second reaction mixture; and isolating a composition comprising L-ornithine phenylacetate from said second reaction mixture.

In some embodiments, the process further comprises stirring the first reaction mixture. In some such embodiments, the stirring step is performed for less than about 90, 80, 70, 60, 50, 40, 30, 20, or 10 minutes, or in a range defined by any two preceding values (for example, between about 10 to about 90 minutes, about 20 to about 80 minutes, about 30 to about 70 minutes, or about 40 to about 60 minutes). In one embodiment, the stirring step is performed for about 60 to 90 minutes. As another non-limiting example, stirring may be performed before and/or after cooling of the first reaction mixture, and before and/or after adding a second solvent to the first reaction mixture. In some embodiments, the stirring time is selected to avoid re-dissolution of precipitated KCl (e.g., a stirring time of sufficiently short duration is selected).

In some embodiments, the process further comprises cooling the first reaction mixture before isolating potassium chloride. In some such embodiments, the first reaction mixture is cooled to less than about 10° C. In one embodiment, the first reaction mixture is cooled to about 0 to 5° C.

In some embodiments of the process described herein, the first solvent comprises or is water. In one embodiment, L-ornithine hydrochloride is added to an aqueous solution of potassium hydroxide. Other non-limiting examples of the first solvent include a mixture of water and one or more polar organic solvents, for example, an alcohol or polyol such as methanol, ethanol, propanol, isopropanol, butanol, isobutanol, tert-butanol, ethylene glycol, propylene glycol, or glycerol.

In some embodiments of the process described herein, the second solvent comprises or is an alcohol. In some such embodiments, the second solvent comprises or is ethanol. Other non-limiting examples of the second solvent include an alcohol or polyol such as methanol, ethanol, propanol, isopropanol, butanol, isobutanol, tert-butanol, ethylene glycol, propylene glycol, or glycerol, or combinations thereof. In addition, the second solvent may also comprise water.

In some embodiments of the process described herein, the first reaction mixture after addition of the second solvent comprises about 1:1 (v/v) to about 1:8 (v/v) first solvent to second solvent. In some such embodiments, the first reaction mixture comprises about 1:1 (v/v) to about 1:8 (v/v) $H_2O$ to ethanol. In particular, the $H_2O$ to ethanol ratio may be selected from about 1:1 (v/v), about 1:2 (v/v), about 1:3 (v/v), about 1:4 (v/v), about 1:5 (v/v), about 1:6 (v/v), about 1:7 (v/v), or about 1:8 (v/v), or in a range defined by any of the two preceding values (for example, about 1:1 (v/v) to about 1:8 (v/v), about 1:2 (v/v) to about 1:7 (v/v), about 1:3 (v/v) to about 1:6 (v/v), or about 1:4 (v/v) to about 1:5 (v/v)). In some embodiments, the ratio of water to ethanol is selected to maintain L-ornithine in solution while minimizing dissolution of KCl. In one embodiment, the water to ethanol ratio is about 1:4.3 (v/v).

In some embodiments of the process described herein, phenylacetic acid is dissolved in a third solvent before intermixing with the first reaction mixture. In some such embodiments, the third solvent comprises or is ethanol. Other non-limiting examples of the third solvent include an alcohol or polyol such as methanol, ethanol, propanol, isopropanol, butanol, isobutanol, tert-butanol, ethylene glycol, propylene glycol, or glycerol, or combinations thereof. In addition, the third solvent may also comprise water.

In some embodiments of the process described herein, the molar ratio of potassium hydroxide to L-ornithine hydrochloride is at least about 1.1:1, at least about 1.15:1, at least about 1.2:1, at least about 1.3:1, at least about 1.4:1, or at least about 1.5:1, or in a range defined by any of the two preceding values. In one embodiment, the molar ratio of potassium hydroxide to L-ornithine hydrochloride is about 1.1:1. In another embodiment, the molar ratio of potassium hydroxide to L-ornithine hydrochloride is about 1.15:1. In still another embodiment, the molar ratio of potassium hydroxide to L-ornithine hydrochloride is about 1.2:1.

In some embodiments of the process described herein, the chloride content of the isolated composition comprising L-ornithine phenylacetate is less than about 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% by weight, or in a range defined by any of the two preceding values (for example, between about 2.5% to about 0.1%, about 2.0% to about 0.5%, or about 1.5% to about 1.0%). Without being bound to any particular theory, it was surprisingly discovered that chloride content of the isolated composition comprising L-ornithine phenylacetate can affect the purification (e.g., recrystallization) of L-ornithine phenylacetate. Specifically, when the L-ornithine phenylacetate composition after initial isolation comprises a chloride content of over about 2.5% to 2.8% by weight, the recrystallization was less efficient. In addition, disproportionation of the organic salt and increase in chloride content (i.e., Cl⁻) can occur. In one embodiment, the chloride content of the composition prepared by the process described herein is less than about 2.5% by weight. In another embodiment, the chloride content of the composition is less than about 1.5% by weight. In yet another embodiment, chloride content of the composition is less than about 1.0% by weight.

In some embodiments of the process described herein, the process further comprises recrystallizing the composition comprising L-ornithine phenylacetate. Recrystallization may be achieved using a single solvent, or a solvent mixture, for example, a mixture of water with one or more polar solvents such as alcohols and/or polyols. As a non-limiting example, the composition is recrystallized from a solvent mixture of water and methanol. In some further embodiments, the volume ratio of water and methanol used in the recrystallization is from about 1:1 to about 1:10, for example, about 1:1, 1:2, 1:3, 1:4, 1:5, 1:6, 1:7, 1:8, 1:9, or 1:10, or a range defined by any two of the preceding values. In one embodiment, the volume ratio of water and methanol is about 1:8. In some embodiments of the process described herein, the chloride content of the recrystallized composition is less than about 0.1% by weight, less than about 0.09%, 0.08%, 0.07%, 0.06%, 0.05%, 0.04%, 0.03%, 0.02% or 0.01% by weight, or in a range defined by any two preceding values (for example, between about 0.01% to about 0.1%, about 0.02% to about 0.09%, about 0.03% to about 0.08%, or about 0.04% to about 0.07%).

In some embodiments of the process described herein, the isolated composition of L-ornithine phenylacetate comprises less than about 5.0%, 4.0%, 3.0%, 2.0%, 1.0%, 0.9%, 0.8%, 0.7%, 0.6%, 0.5%, 0.4%, 0.3%, 0.2% or 0.1% L-ornithine cyclization or dimerization side products, or a range defined by any two of the preceding values. Certain side products may be formed during the manufacturing of L-ornithine phenylacetate. For example, cyclization of L-ornithine lead to the formation of a lactam (i.e., (S)-3-aminopiperidin-2-one), which is known to be a significant side product in preparation protocols that involve elevated temperatures. In addition, it is known that amino acids like L-ornithine can dimerize under certain conditions, such as in basic condition at elevated temperature where two molecules of L-ornithine can undergo intermolecular condensation. The process described herein eliminate the need of using any distillation at elevated temperature to isolate L-ornithine phenylacetate, thereby reducing or preventing the formation of any L-ornithine cyclization or dimerization side products. In some embodiments, the isolated composition comprises less than about 1.0% L-ornithine cyclization or dimerization side products. In some further embodiments, the isolated composition is substantially free or free of L-ornithine cyclization or dimerization side products.

Pharmaceutical Compositions of L-Ornithine Phenylacetate

Some embodiments disclosed herein include a composition comprising L-ornithine phenylacetate, in particular a composition prepared by the process described herein. In some embodiments, the composition has a chloride content of less than about 1.5% by weight, and in some embodiments, the composition is free of silver ion, benzoic acid or salts thereof. In some further embodiments, the composition has a chloride content less than about 1.4%, 1.3%, 1.2%, 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% by weight, or in a range defined by any two of the preceding values (for example, between about 1.5% and about 0.01%, about 1.2% to about 0.05%, or about 1.0% to about 0.1%). In one embodiment, the composition has a chloride content of less than about 0.1% by weight. In some embodiments, the composition comprises less than about 1.0% L-ornithine cyclization or dimerization side products. In some further embodiments, the composition comprises less than about 1.0%, 0.9%, 0.8%, 0.7%, 0.6%, 0.5%, 0.4%, 0.3%, 0.2% or 0.1% L-ornithine cyclization or dimerization side products. In some further embodiments, the composition is substantially free or free of L-ornithine cyclization or dimerization side products.

In some embodiments, the composition comprises one or more crystalline forms of L-ornithine phenylacetate, or combinations thereof. Various crystalline forms of L-ornithine phenylacetate have been disclosed in U.S. Publication No. 2010/0280119, which is incorporated by reference. In particular, crystalline forms of L-ornithine phenylacetate include Form I (exhibiting XRPD characteristic peaks at approximately 4.9°, 13.2°, 17.4°, 20.8° and 24.4° 2θ), Form II (exhibiting XRPD characteristic peaks at approximately 6.0°, 13.9°, 14.8°, 17.1°, 17.8° and 24.1° 2θ), or Form III (exhibiting XRPD characteristic peaks at approximately 5.8°, 14.1°, 18.6°, 19.4°, 22.3° and 24.8° 2θ). As is well understood in the art, because of the experimental variability when X-ray diffraction patterns are measured on different instruments, the peak positions are assumed to be equal if the two theta (2θ) values agree to within 0.2° (i.e., ±0.2°).

The compositions of L-ornithine phenylacetate of the present disclosure may be formulated for administration to a subject (e.g., a human). L-Ornithine phenylacetate, and accordingly the compositions disclosed herein, may be formulated for administration with a pharmaceutically acceptable carrier or diluent. L-ornithine phenylacetate may thus be formulated as a medicament with a standard pharmaceutically acceptable carrier(s) and/or excipient(s) as is routine in the pharmaceutical art. The exact nature of the formulation will depend upon several factors including the desired route of administration. Typically, L-ornithine phenylacetate is formulated for oral, intravenous, intragastric, subcutaneous, intravascular or intraperitoneal administration.

The pharmaceutical carrier or diluent may be, for example, water or an isotonic solution, such as 5% dextrose in water or normal saline. Solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical compositions. Such pharmaceutical preparations may be manufactured in known manners, for example, by means of mixing, granulating, tableting, sugar-coating, or film-coating processes. The solid oral forms may provide immediate release or controlled release of L-ornithine phenylacetate.

Liquid dispersions for oral administration may be syrups, emulsions or suspensions. The syrups may contain as carriers, for example, saccharose or saccharose with glycerine and/or mannitol and/or sorbitol. Suspensions and emulsions may contain a carrier, for example a natural gum, agar, sodium alginate, pectin, methylcellulose, carboxymethylcellulose, or polyvinyl alcohol.

The pharmaceutical composition may consist essentially of L-ornithine phenylacetate and a pharmaceutically acceptable carrier. Such a pharmaceutical composition therefore contains substantially no other amino acids in addition to L-ornithine and phenylacetate. Furthermore, such a pharmaceutical composition contains insubstantial amounts of other salts in addition to L-ornithine phenylacetate.

Oral formulations may generally include dosages of L-ornithine phenylacetate in the range of about 500 mg to about 50 g. In some embodiments, L-ornithine phenylacetate is in a low dosage of about 0.1 g to about 10 g. In some embodiments, the L-ornithine phenylacetate is in a dosage of about 2.0 g, about 2.5 g, about 3.0 g, about 3.5 g, about 4.0 g, about 4.5 g, about 5.0 g, about 5.5 g, about 6.0 g, about 6.5 g, about 7.0 g, about 7.5 g, about 8.0 g, about 8.5 g, about 9.0 g, about 9.5 g, or about 10.0 g, or in a dosage range defined by any of the two preceding values (for example, 5.0 g to 8.0 g). In some embodiments, the pharmaceutical formulation is in a single unit dosage form. In some other embodiments, the pharmaceutical formulation is in two or more unit dosage forms (i.e., a divided dose). In one embodiment, the oral dosage is about 2.5 g. In another embodiment, the oral dosage is about 5 g.

Intravenous formulations may also generally include dosages of L-ornithine phenylacetate in the range of about 500 mg to about 50 g (preferably about 1 g to about 25 g, about 2.0 g to about 20 g, or about 2.5 g to about 10 g). In some embodiments, the intravenous formulation has a concentration of about 5 to about 300 mg/mL of L-ornithine phenylacetate (preferably about 25 to about 200 mg/mL, and more preferably about 40 to about 60 mg/mL).

The pharmaceutical composition may optionally be placed is sealed packaging. The sealed packaging may reduce or prevent moisture and/or ambient air from contacting the composition or medicament. In some embodiments, the packaging includes a hermetic seal. In some embodiments, the packaging sealed under vacuum or with an inert gas (e.g., argon) within the sealed package. Accordingly, the packaging can inhibit or reduce the rate of degradation for the composition or medicament stored within the packaging. Various types of sealed packaging are known in the art. For example, U.S. Pat. No. 5,560,490, is hereby incorporated by reference in its entirety, discloses an exemplary sealed package for medicaments.

The composition, in some embodiments, may further include a sufficiently low chloride content. As a non-limiting example, the chloride content of the composition comprising L-ornithine phenylacetate may be less than about 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01%, by weight. In addition, the pharmaceutical composition can be free of silver ions, benzoic acid or salts thereof, or L-ornithine cyclization or dimerization side product.

Methods of Treatment

Some embodiments of the present disclosure relate to methods of treating or ameliorating hyperammonemia comprising orally administering to a subject in need thereof a pharmaceutical composition comprising an effective amount of L-ornithine phenylacetate as described herein. In some embodiments, the subject has acute liver failure or chronic liver diseases. In some embodiments, the subject has liver cirrhosis or liver decompensation. In some such embodiments, the chronic liver disease or liver cirrhosis has a classification of Child-Pugh class A, B or C. In some embodiments, the subject has hepatic encephalopathy. In still some embodiments, the subject has portal hypertension. In some embodiments, the subject has a urea cycle disorder.

In some embodiments, L-ornithine phenylacetate is administered in an amount from about 0.1 g to about 50 g per day, from about 0.5 g to about 45 g per day, from about 1 g to about 40 g per day, from about 1.5 g to about 35 g per day, from about 2 g to about 30 g per day, from about 2.5 g to about 25 g per day, from about 3 g to about 20 g per day, or from about 5 g to about 15 g per day. In some embodiments, the pharmaceutical composition is for administration at least once a day. In some further embodiments, the pharmaceutical composition is for administration two or more times per day.

EXAMPLES

The following examples, including experiments and results achieved, are provided for illustrative purposes only and are not to be construed as limiting the present application.

Example 1: Large-Scale Batch Process to Produce Crude L-Ornithine Phenylacetate

A first reactor was charged with 4.05 kg (61.38 moles) of KOH, which was dissolved in 10.4 L (10.4 kg) $H_2O$ and stirred until a clear solution was formed. Subsequently, 9.00 kg (53.37 moles) of L-ornithine HCl was added to the KOH solution in two portions at about 15-25° C. to create a suspension. Subsequently, 45.0 L (35.5 kg) ethanol was added to the suspension at 15-25° C., and stirred for approximately 15-20 minutes. The suspension was then cooled to about 0-5° C. and stirred at that temperature for at least 60 minutes, but no longer than 90 minutes. Separately, 8.72 kg (64.05 mol) of phenylacetic acid (PAA) was dissolved in 36.0 L (28.4 kg) of ethanol and stirred at 15-25° C. until full dissolution occurred in a second reactor. The cold suspension of the first reactor was filtered into the solution of PAA through depth filtration to remove the precipitated KCl, and the filter cake was washed with about 18.0 L (14.2 kg) of ethanol at 0-5° C. The reaction mixture was stirred at 15-25° C. for about 15-30 minutes and a thick white suspension formed. The reaction mixture was concentrated in vacuo at 45-55° C. (azeotropic distillation) to reach a final volume of about 90 L, which was stirred for at least 2 hours at 15-25° C. The suspension was filtered to obtain the crude L-ornithine phenylacetate, which was then washed with 36.0 L (28.4 kg) of ethanol, and dried in vacuo at approximately 50° C. for at least 12 hours. Yield: 88.4% (14.00 kg) calculated based on the assay data from chloride titration.

In this process, azeotropic distillation on scale performed poorly, giving approx. 10% $H_2O$ in the mother liquor of the suspension after the first cycle. After the second distillation the mixture was stirred overnight. It was observed that the water level was relatively low and that significant precipitation of salts (shown by the high $Cl^-$ level in filtered and dried product) had occurred during that time. Adjustment of the water level in the slurry by addition of extra water did not restore the desired chloride distribution in the system and the crude product was isolated afterwards. It is presumed that the combination of the low water level (3% vs. 8%) and the longer stirring time (16 hours vs. 2 hours) was responsible for the precipitation of KCl. Surprisingly, the high salt content in the crude product did not affect its stoichiometry (determined by 1H-NMR in $D_2O$—1.000:1.002 (PAA/L-ORN)). Laboratory experiments with material derived from IPC samples revealed that a reduction of the chloride level in the crude product by conventional recrystallization was not successful as the chloride content of the crude product was 4.57% by weight. Hence, the batch was not recrystallized on scale.

Example 2: Improved Large-Scale Batch Process to Produce Crude L-Ornithine Phenylacetate A first reactor (100 L) was charged with 4.05 kg (61.38 moles) of KOH, which was dissolved in 10.4 L (10.4 kg) H$_2$O and stirred until a clear solution was formed. Subsequently, 9.00 kg (53.37 moles) of L-ornithine HCl was added to the KOH solution in two portions at about 15-25° C. to create a suspension. Subsequently, 45.0 L (35.5 kg) ethanol was added to the suspension at 15-25° C., and stirred for approximately 15-20 minutes. The suspension was then cooled to about 0-5° C. and stirred at that temperature for at least 60 minutes, but no longer than 90 minutes. Separately, 8.72 kg (64.05 mol) of phenylacetic acid (PAA) was dissolved in 36.0 L (28.4 kg) of ethanol and stirred at 15-25° C. until full dissolution occurred in a second reactor (450 L). The cold suspension of the first reactor was filtered into the solution of PAA through depth filtration to remove the precipitated KCl, and the filter cake was washed with about 36.0 L (28.4 kg) of ethanol at 0-5° C. The reaction mixture was stirred for approximately 2 hours at 15-25° C., and a thick, white suspension was formed. The suspension was isolated with a centrifuge to obtain the crude L-ornithine phenylacetate, which was then washed with 36.0 L (28.4 kg) of ethanol, and dried in vacuo at approximately 50° C. for at least 10 hours. Yield: 95.1% (13.62 kg); not corrected for assay. The crude L-ornithine phenylacetate contained about 1.28% by weight of chloride (Cl$^-$).

The process of Example 2 is illustrated in the scheme below:

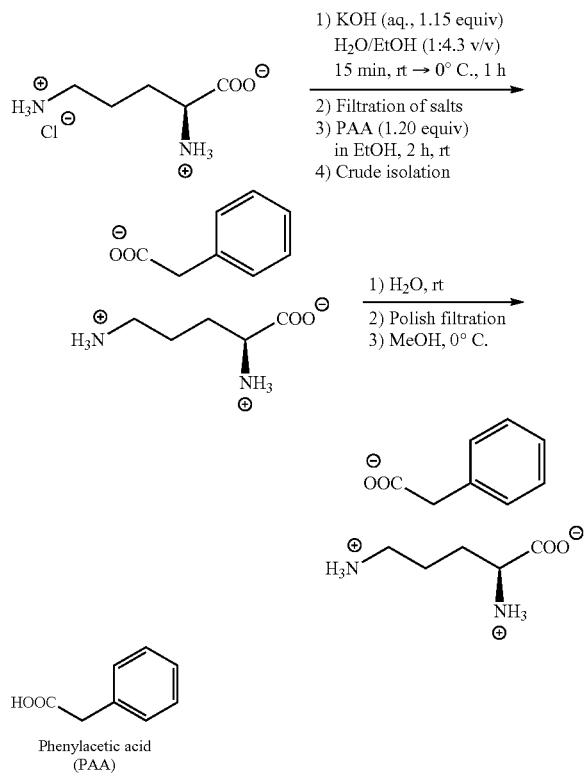

Example 3: Recrystallization of L-Ornithine Phenylacetate 13.12 kg (48.89 moles) of the crude L-ornithine phenylacetate of Example 2 was added followed by addition of 32.8 L (32.8 kg) of H$_2$O in a first container, and stirred for approximately 15-30 minutes at 15-25° C. until full dissolution. The resulting solution was then filtered through a particle filter (0.2 µm) into a second container. The particle filter was washed with 262.4 L (207.8 kg) methanol into the second container and a suspension forms. The suspension was cooled to 0-5° C. and stirred for approximately 60 minutes at 0-5° C., but stirred no longer than 90 minutes. A crystalline solid (L-ornithine phenylacetate) precipitated after cooling. The precipitate was isolated by centrifuge and washed with 52.5 L (42.6 kg) of methanol. The final product was dried in vacuo at approximately 50° C. for at least 10 hours. The dried product was delumped via milling (sieve of 1.0 mm). Yield: 70.5% overall (9.72 kg) (74.1% yield for recrystallization only). The recrystallized L-ornithine phenylacetate contained about 0.08% by weight of chloride (Cl$^-$).

What is claimed is:

1. A process of making L-ornithine phenylacetate, comprising:
    intermixing L-ornithine hydrochloride and potassium hydroxide in a first solvent to form a first reaction mixture, wherein the first solvent comprises water;
    adding a second solvent to said first reaction mixture, wherein the second solvent comprises ethanol;
    isolating potassium chloride from said first reaction mixture;
    intermixing phenylacetic acid with said first reaction mixture to form a second reaction mixture; and
    isolating a composition comprising L-ornithine phenylacetate from said second reaction mixture.

2. The process of claim 1, further comprising cooling said first reaction mixture before isolating potassium chloride.

3. The process of claim 2, wherein said first reaction mixture is cooled to about 0 to 5° C.

4. The process of claim 1, wherein said first solvent is water.

5. The process of claim 1, wherein said second solvent is ethanol.

6. The process of claim 1, wherein the first reaction mixture after addition of the second solvent comprises about 1:1 (v/v) to 1:8 (v/v) water to ethanol.

7. The process of claim 1, wherein phenylacetic acid is dissolved in a third solvent before intermixing with said first reaction mixture.

8. The process of claim 7, wherein said third solvent comprises ethanol.

9. The process of claim 1, wherein the molar ratio of potassium hydroxide to L-ornithine hydrochloride is at least about 1.1:1.

10. The process of claim 1, wherein the molar ratio of phenylacetic acid to L-ornithine hydrochloride is at least about 1.2:1.

11. The process of claim 1, wherein the chloride content of the composition comprising L-ornithine phenylacetate is less than about 2.5% by weight.

12. The process of claim 1, further comprising recrystallizing the composition comprising L-ornithine phenylacetate.

13. The process of claim 12, wherein the composition is recrystallized from a solvent mixture of water and methanol.

14. The process of claim 13, wherein the volume ratio of water and methanol used in the recrystallization is from about 1:1 to about 1:10.

15. The process of claim 12, wherein the chloride content of the recrystallized composition is less than about 0.1% by weight.

16. The process of claim 1, wherein said composition comprises less than about 5.0% L-ornithine cyclization or dimerization side products.

17. The process of claim 1, wherein said composition is free of L-ornithine cyclization or dimerization side products.

18. The process of claim 6, wherein the first reaction mixture after addition of the second solvent comprises about 1:4 (v/v) water to ethanol.

\* \* \* \* \*